(12) United States Patent
Bharat et al.

(10) Patent No.: US 11,166,700 B2
(45) Date of Patent: Nov. 9, 2021

(54) OPTIMAL ULTRASOUND-BASED ORGAN SEGMENTATION

(71) Applicant: KONINKLIJKE PHILIPS N.V., Eindhoven (NL)

(72) Inventors: Shyam Bharat, Arlington, MA (US); Amir Mohammad Tahmasebi Maraghoosh, Melrose, MA (US); Jean-Luc Robert, Cambridge, MA (US); Dirk Binnekamp, Borne (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 761 days.

(21) Appl. No.: 15/560,055

(22) PCT Filed: Mar. 15, 2016

(86) PCT No.: PCT/IB2016/051454
§ 371 (c)(1),
(2) Date: Sep. 20, 2017

(87) PCT Pub. No.: WO2016/151428
PCT Pub. Date: Sep. 29, 2016

(65) Prior Publication Data
US 2018/0070923 A1 Mar. 15, 2018

Related U.S. Application Data

(60) Provisional application No. 62/138,075, filed on Mar. 25, 2015, provisional application No. 62/169,577, filed on Jun. 2, 2015.

(51) Int. Cl.
*A61B 8/08* (2006.01)
*A61B 8/00* (2006.01)
(Continued)

(52) U.S. Cl.
CPC .............. *A61B 8/5223* (2013.01); *A61B 8/14* (2013.01); *A61B 8/463* (2013.01); *A61B 8/469* (2013.01);
(Continued)

(58) Field of Classification Search
CPC . G06T 7/10; G06T 2207/10132; A61B 8/463; A61B 8/14; A61B 8/5269;
(Continued)

(56) References Cited

U.S. PATENT DOCUMENTS

| 6,390,984 B1 | 5/2002 | Pan et al. |
| 2006/0274928 A1 | 7/2006 | Jeffrey |

(Continued)

FOREIGN PATENT DOCUMENTS

| EP | 2645329 A1 | 10/2013 |
| WO | 2012017375 A2 | 2/2012 |

(Continued)

OTHER PUBLICATIONS

"A Survey of Prostate Segmentation Methodologies in Ultrasound, Magnetic Resonance and Computed Tomography Images"; Ghose, et al.; vol. 108, Issue 1, Oct. 2012, pp. 262-287.

*Primary Examiner* — Bo Joseph Peng

(57) ABSTRACT

A segmentation selection system includes a transducer (14) configured to transmit and receive imaging energy for imaging a subject. A signal processor (26) is configured to process imaging data received to generate processed image data. A segmentation module (50) is configured to generate a plurality of segmentations of the subject based on features or combinations of features of the imaging data and/or the processed image data. A selection mechanism (52) is configured to select one of the plurality of segmentations that best meets a criterion for performing a task.

11 Claims, 4 Drawing Sheets

(51) Int. Cl.
    *G06T 7/10*    (2017.01)
    *G06K 9/20*    (2006.01)
    *A61B 8/14*    (2006.01)
    *G06K 9/40*    (2006.01)
    *G06K 9/46*    (2006.01)

(52) U.S. Cl.
    CPC .......... *A61B 8/5207* (2013.01); *A61B 8/5269* (2013.01); *G06K 9/209* (2013.01); *G06T 7/10* (2017.01); *G06K 9/40* (2013.01); *G06K 9/4604* (2013.01); *G06K 2209/051* (2013.01); *G06T 2207/10132* (2013.01)

(58) Field of Classification Search
    CPC ..... A61B 8/5223; A61B 8/5207; A61B 8/469; G06K 9/209; G06K 9/4604; G06K 9/40; G06K 2209/051
    See application file for complete search history.

(56) References Cited

U.S. PATENT DOCUMENTS

2006/0235301 A1* 10/2006 Chalana .................. G06K 9/32
                                                    600/443
2010/0081931 A1*  4/2010 Destrempes ............. G06T 7/12
                                                    600/437
2014/0003686 A1   1/2014 Fontanarosa

FOREIGN PATENT DOCUMENTS

| WO | 2012176100 | A1 | 12/2012 |
| WO | 2013104970 | A1 | 7/2013 |
| WO | 2014096041 | A3 | 6/2014 |

* cited by examiner

OPTIMAL ULTRASOUND-BASED ORGAN SEGMENTATION

CROSS-REFERENCE TO PRIOR APPLICATIONS

This application is the U.S. National Phase application under 35 U.S.C. § 371 of International Application No. PCT/IB2016/051454, filed on Mar. 15, 2016, which claims the benefit of U.S. Provisional Patent Application No. 62/138,075, filed on Mar. 25, 2015, and U.S. Provisional Patent Application No. 62/169,577, filed on Jun. 2, 2015. These applications are hereby incorporated by reference herein.

BACKGROUND

Technical Field

This disclosure relates to medical instruments and more particularly to systems, methods and user interfaces for image component segmentation for imaging applications.

Description of the Related Art

Ultrasound (US) is a low-cost, easy-to-use imaging modality that is widely used for intra-procedural real-time guidance and treatment monitoring. Ultrasound image segmentation is mainly driven by the clinical need for extracting organ boundaries in B-mode images as a step towards dimension measurement (e.g., tumor size and extent). The appearance of geometric boundaries of organs in US images mainly depends on the acoustic impedance between tissue layers. Despite its low cost and ease-of-use, US B-mode imaging is not necessarily the most suitable for anatomical imaging. B-mode US images, compared to other imaging modalities, such as, magnetic resonance (MR) and computed tomography (CT), suffer from poor signal-to-noise ratio and background speckle noise. Existing ultrasound-based segmentation methods utilize pixel (or voxel, in 3D) information from the B-mode images as input to a metric calculator (where 'metric' refers to the quantity calculated, namely, signal-to-noise ratio (SNR), contrast, texture etc.).

US B-mode images are also afflicted with the problem of poor contrast between an organ and its immediately surrounding tissue (e.g., prostate-bladder, prostate-rectal wall) due to isoechoic pixel values on the B-mode images. This limits the robustness of many existing automated segmentation methods. Manual segmentation remains the only possible alternative, and the achievable accuracy with this method is heavily dependent on the skill-level of the clinician. The inter-operator variability in manual US segmentation is on the order of 5 mm, with the Dice coefficient (a measure of similarity) being 20-30% lower than for MRI segmentations.

SUMMARY

In accordance with the present principles, a segmentation selection system includes a transducer configured to transmit and receive imaging energy for imaging a subject. A signal processor is configured to process imaging data received to generate processed image data. A segmentation module is configured to generate a plurality of segmentations of the subject based on features or combinations of features of the imaging data and/or the processed image data. A selection mechanism is configured to select one of the plurality of segmentations that best meets a criterion for performing a task.

Another segmentation selection system includes an ultrasound transducer configured to transmit and receive ultrasound energy for imaging a subject. A B-mode processor is configured to process imaging data received to generate processed image data. A segmentation module is configured to generate a plurality of segmentations of the subject based on one or more combinations of input data and segmentation metrics. A graphical user interface permits a user to select features or combinations of features of imaging data and/or processed image data to generate the plurality of segmentations and to select a segmentation that best meets criterion for performing a task.

A method for segmentation selection includes receiving imaging energy for imaging a subject; image processing data received to generate processed image data; generating a plurality of segmentations of the subject based on features or combinations of features of raw imaging data and/or processed imaging data; and selecting at least one of the plurality of segmentations that best meets a segmentation criterion.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
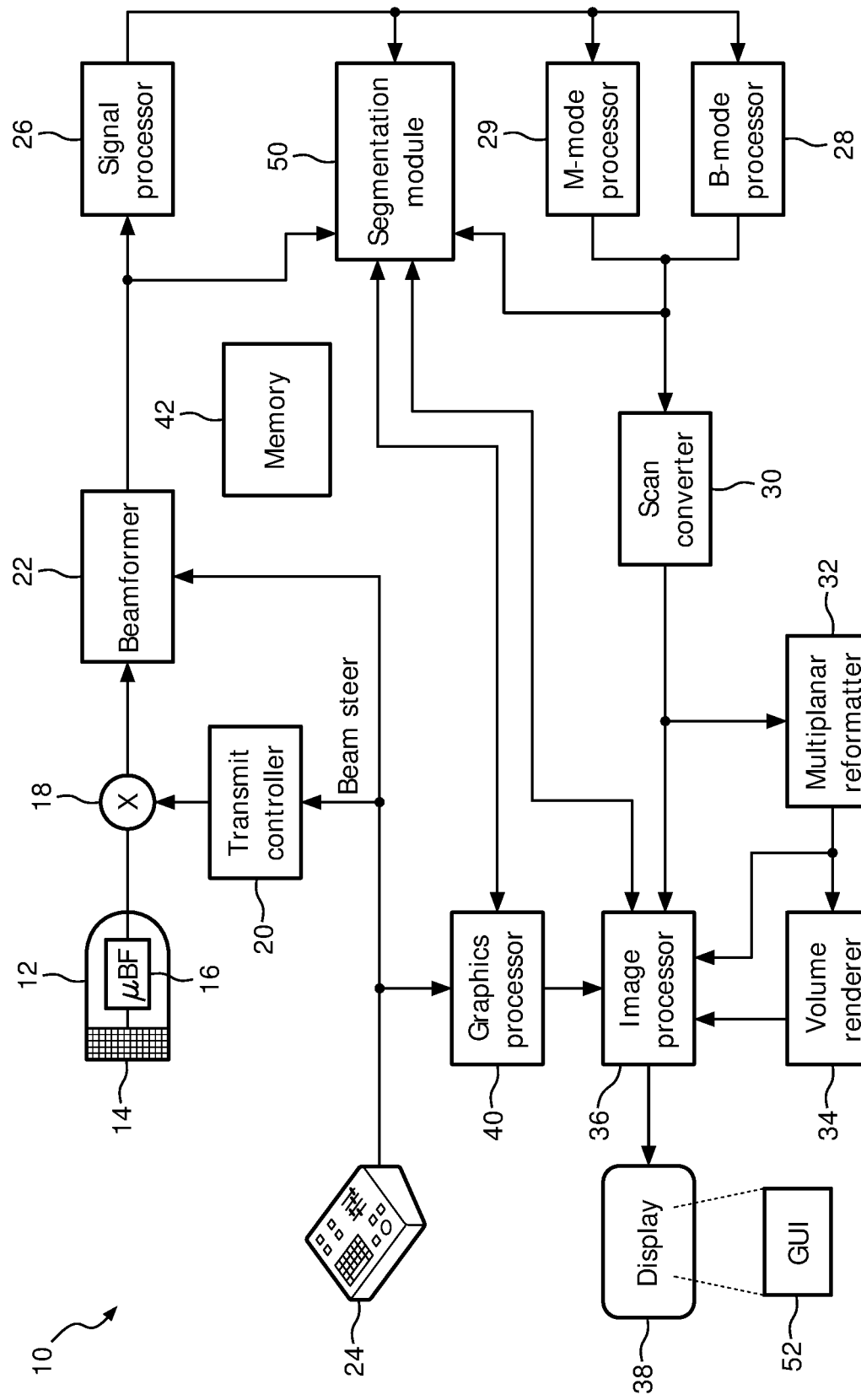
FIG. 1 is a block/flow diagram showing an imaging system with a segmentation selection module in accordance with one embodiment.

In accordance with the present principles, systems and methods are provided to estimate an optimal segmentation from multiple segmentations of a single imaging modality (e.g., ultrasound (US)). The multiple segmentations may employ, e.g., raw beam-summed US radiofrequency (RF) data and/or other data matrices along the pipeline of B-mode (brightness mode) image formation, in conjunction with various segmentation metrics. Both manual and automatic methods may be selectable by a user through a user interface to choose the optimal segmentation.

Ultrasound B-mode images are created by detecting an envelope of raw RF data, followed by logarithmic compression and scan conversion. The logarithmic data compression permits concurrent visualization of a wide range of echoes. However, this also suppresses subtle variations in image contrast that may be vital to achieving an accurate segmentation. In accordance with the present principles, a computation of segmentation metrics is provided on different US data forms (prior to the generation of conventional B-mode data). The segmentation will be derived from one or more metrics (texture, contrast, etc.). Based on the data matrix and segmentation metric used, multiple segmentation outputs will be presented to the user, with the possibility of manually or automatically choosing the optimal segmentation. The chosen segmentation will be superimposed on the B-mode image visualized on the screen, without adding any complexity from the user's perspective. Overall, the unprocessed RF data is potentially rich in information about the organ under investigation and the boundaries between tissues. Involving several different data streams in the segmentation process, complementary to the B-mode image, can lead to a more accurate segmentation that is less sensitive to speckle noise. Hence, the computation of multi-channel segmentation metrics on pre-log compressed data is provided. The present principles increase the accuracy and robustness of segmentation algorithms, thereby improving and streamlining clinical workflow.

It should be understood that the present invention will be described in terms of medical instruments for US imaging; however, the teachings of the present invention are much broader and are applicable to any imaging modality where multiple segmentation options can be provided for that modality. In some embodiments, the present principles are employed in tracking or analyzing complex biological or mechanical systems. In particular, the present principles are applicable to internal tracking procedures for biological systems, and may include procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, an ultrasound imaging system 10 constructed in accordance with the present principles is shown in block diagram form. The ultrasound system 10 includes a transducer device or probe 12 having a transducer array 14 for transmitting ultrasonic waves and receiving echo information. The transducer array may be configured as, e.g., linear arrays or phased arrays, and can include piezoelectric elements or capacitive micromachined ultrasonic transducers (CMUT) elements. The transducer array 14, for example, can include a two dimensional array of transducer elements capable of scanning in both elevation and azimuth dimensions for 2D and/or 3D imaging.

The transducer array 14 is coupled to a microbeamformer 16 in the probe 12, which controls transmission and reception of signals by the transducer elements in the array. The microbeamformer 16 may be integrated with the flexible transducer device 12 and is coupled to a transmit/receive (T/R) switch 18, which switches between transmission and reception and protects a main beamformer 22 from high energy transmit signals. In some embodiments, the T/R switch 18 and other elements in the system can be included in the transducer probe rather than in a separate ultrasound system base. The transmission of ultrasonic beams from the transducer array 14 under control of the microbeamformer 16 is directed by a transmit controller 20 coupled to the T/R switch 18 and the beamformer 22, which may receive input from the user's operation of a user interface or control panel 24.

One function controlled by the transmit controller 20 is the direction in which beams are steered. Beams may be steered straight ahead from (orthogonal to) the transducer array 14, or at different angles for a wider field of view. The partially beamformed signals produced by the microbeamformer 16 are coupled to a main beamformer 22 where partially beamformed signals from individual patches of transducer elements are combined into a fully beamformed signal.

The beamformed signals are coupled to a signal processor 26. The signal processor 26 can process the received echo signals in various ways, such as bandpass filtering, decimation, I and Q component separation, and harmonic signal separation. The signal processor 26 may also perform additional signal enhancement such as speckle reduction, signal compounding, and noise elimination. The processed signals are coupled to a B mode processor 28 or other mode processor, e.g., an M-mode processor 29), which can employ amplitude detection for the imaging of structures in the body. The signals produced by the mode processors 28, 29 are coupled to a scan converter 30 and a multiplanar reformatter 32. The scan converter 30 arranges the echo signals in the spatial relationship from which they were received in a desired image format. For instance, the scan converter 30 may arrange the echo signal into a two dimensional (2D) sector-shaped format, or a pyramidal three dimensional (3D) image. The multiplanar reformatter 32 can convert echoes which are received from points in a common plane in a volumetric region of the body into an ultrasonic image of that plane.

A volume renderer 34 converts the echo signals of a 3D data set into a projected 3D image as viewed from a given reference point. The 2D or 3D images are coupled from the scan converter 30, multiplanar reformatter 32, and volume renderer 34 to an image processor 36 for further enhancement, buffering and temporary storage for display on an image display 38. A graphics processor 40 can generate graphic overlays for display with the ultrasound images. These graphic overlays or parameter blocks can contain, e.g., standard identifying information such as patient name, date and time of the image, imaging parameters, frame indices and the like. For these purposes, the graphics processor 40 receives input from the user interface 24, such as a typed patient name. The user interface 24 can also be coupled to the multiplanar reformatter 32 for selection and control of a display of multiple multiplanar reformatted (MPR) images.

In accordance with the present principles, ultrasound data is acquired and stored in memory 42. The memory 42 is depicted as being centrally placed; however, the memory 42 may store data and interact at any position in the signal path. Corrections may be employed as feedback for correcting a beam steering signal (Beam Steer) in accordance with the positions of the elements in the array 14.

Display 38 is included for viewing internal images of a subject (patient) or volume. Display 38 may also permit a user to interact with the system 10 and its components and functions, or any other element within the system 10. This is further facilitated by the interface 24, which may include a keyboard, mouse, a joystick, a haptic device, or any other peripheral or control to permit user feedback from and interaction with the system 10.

Ultrasound B-mode images are output from the B-mode processor 28 and are created by detecting an envelope of raw RF data, followed by logarithmic compression and scan conversion by the scan converter 30. The logarithmic data compression by the B-mode processor 28 permits concurrent visualization of a wide range of echoes.

Ultrasound M-mode images are output from an M-mode processor 29. M-mode images may be processed (e.g., compressed) and sent for scan conversion by the scan converter 30. In M-mode (motion mode) ultrasound, pulses are emitted in quick succession when A-mode or B-mode images are taken to record successive images. As the organ boundaries produce reflections relative to the probe 12, this can be used to determine the velocity of specific organ structures.

A computation of segmentation metrics is provided on different US data forms (prior to the generation of conventional B-mode data or M-mode data) and received by a segmentation module 50. The segmentation module 50 derives a plurality of segmentation images generated from one or more metrics (e.g., texture, contrast, etc.) measured from the US data. Based on the data matrix and segmentation metric employed, multiple segmentation outputs will be generated using the image processor 36 (or graphics processor 40) for display on the display 38. The segmentation outputs are presented to the user on a graphical user interface (GUI) 52 generated by the image processor 36 (or the graphics processor 40).

The segmentation outputs are presented to the user with the possibility of manually or automatically choosing an optimal segmentation. The chosen segmentation may be superimposed on the B-mode image visualized on the display 38 by the image processor 36 (or the graphics processor 40). The unprocessed RF data provided prior to B-mode processing 28 (or even before signal processing 26) is potentially rich in information about an organ or region under investigation and boundaries between tissues. Introducing several different data types into the segmentation process by the segmentation module 50 can be complementary to the B-mode image from the B-mode processor 28 and can lead to a more accurate segmentation that is less sensitive to speckle noise or other image degradation phenomena. Hence, the computation of multi-channel segmentation metrics on pre-log compressed data can increase the accuracy and robustness of segmentation algorithms, thereby improving and streamlining clinical workflow.

The image processor 36 is configured to generate a graphical user interface (GUI) or other selection mechanism 52 for user selection of an optimal segmentation. The segmentation module 50 provides different segmentation outputs resulting from multiple combinations of input data and segmentation metrics to determine an optimal segmentation for an application at hand. Optimality can change based on the organ being segmented and the task at hand. Input data refers to the use of different forms of US data in segmentation algorithms and include but are not limited to the following potential possibilities, e.g., raw beam-summed RF data, prior to envelope detection and logarithmic compression, envelope-detected data, formed from raw beam-summed RF data, B-mode images, formed without logarithmic compression, B-mode images, formed without logarithmic compression and without application of other filters, conventional B-mode images, M-mode images, etc. Segmentation metrics refer to a quantity used to characterize tissue regions, e.g., Signal-to-Noise Ratio (SNR), contrast, texture, model-driven algorithms, etc. In some cases, optimality can be a subjective measure that is decided by the user.

The different segmentations obtained will then be presented to the user on a display 38 through, e.g., GUI 52, for manual selection of the optimal segmentation. Automatic selection of the optimal segmentation is also contemplated as will be described. The image processor 36 (or graphics processor 40) provides visualizations of the segmentations. The different segmentation outputs are superimposed on the original B-mode image, to permit the user to choose the best segmentation. In one embodiment, the image processor 36 automatically cycles through different segmentation results periodically. In another embodiment, all outputs may concurrently be visualized in a color-coded or other visual format. If automatic selection of the optimal segmentation is performed, the selected optimal segmentation will be superimposed on the B-mode image shown on the display 38.

Figure 2:
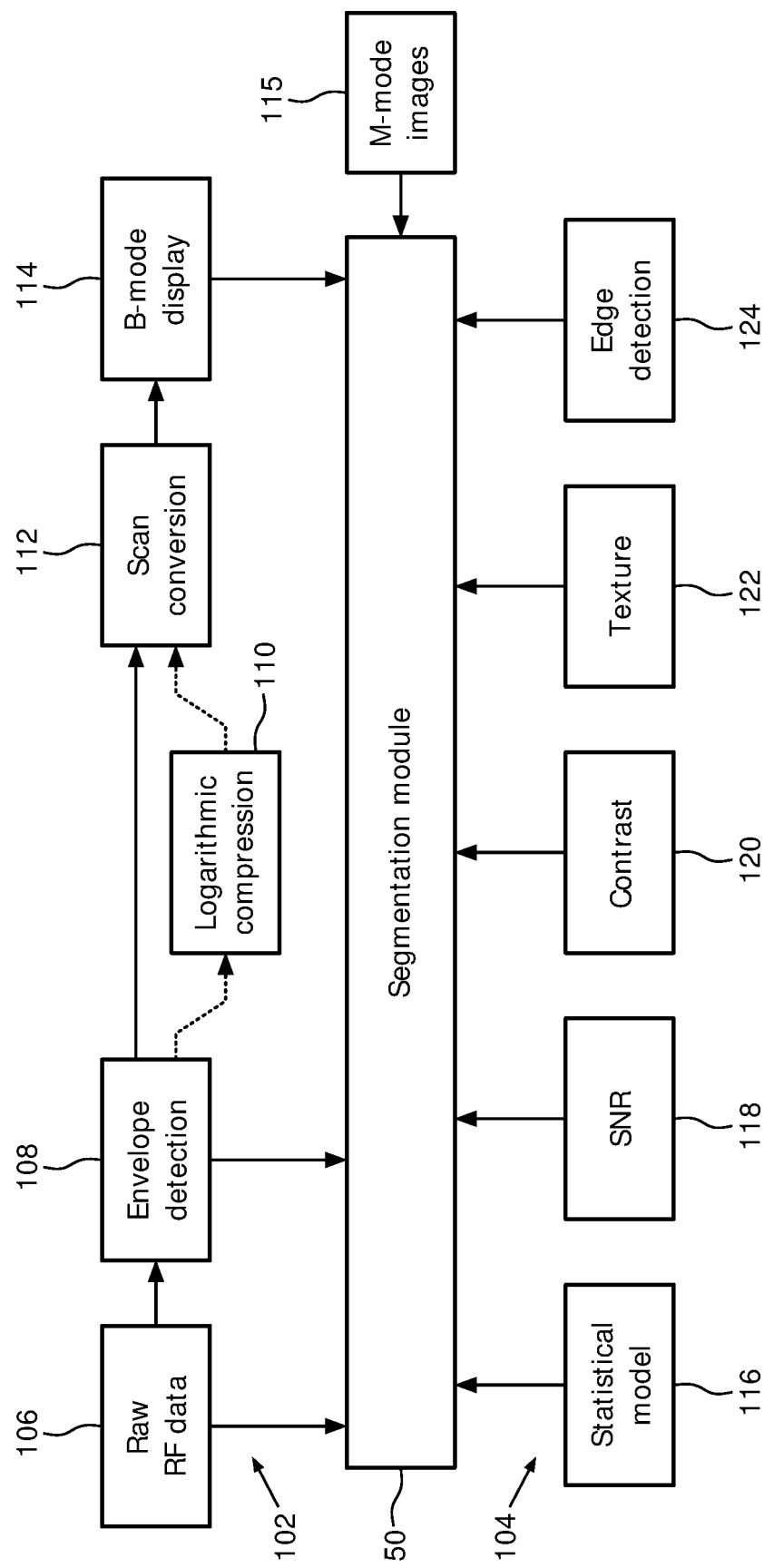
FIG. 2 is a block/flow diagram showing data or signal inputs to a segmentation selection module for generating a plurality of segmentations in accordance with one embodiment.

Referring to FIG. 2, a block/flow diagram illustratively shows two sets of inputs to the segmentation module 50 where input data 102 and segmentation metrics 104 are depicted. Inputs to the segmentation module 50 show a pipeline of US B-mode image formation where uncompressed data is employed at various stages of the pipeline. A specific combination input data 102 and segmentation metrics 104 will provide the 'optimal' segmentation for a particular organ site, US system capabilities, etc. The input data 102 may include raw RF data 106 (from anywhere in the signal path prior to the B-mode processor 28, FIG. 1), envelope detection data 108 (from signal envelope (carrier waves)) and from a B-mode display 114 (B-mode images or image data). M-mode images or data 115 (or other image modes) may also be employed as input data. The B-mode or M-mode images may be derived from a scan conversion 112 with or without logarithmic compression 110. The segmentation metrics 104 may include statistical models 116 or the US imaged volume, SNR 118, contrast 120, texture 122, edge detection 124 or any other image characteristics.

For the input data 102, the logarithmic compression of the data used is avoided to employ the entire range of the information captured for calculation of the segmentation metric 104. Multiple segmentations may be provisioned from which the 'optimal' or 'best' segmentation can be selected by the segmentation module 50. This selection can be made automatically or manually.

For an automatic selection of the optimal segmentation, appropriate criteria may be defined. Examples of potential criteria that may be used include, e.g., Whether the segmented volume is at least 'x' $cm^3$?; Does the segmented volume include certain pre-annotated anatomical landmarks?; Does the segmented volume differ from the mean population-based segmentation model by greater than 'x' %?; Does the segmented shape differ from the mean population-based shape model by greater than 'x' %?; etc. The metrics that are not utilized to generate the segmentation may be utilized to rate the quality of the segmentation.

For a manual selection of the optimal segmentation, the different segmentations can be presented to the user by superimposing them on the B-mode image(s), e.g., all segmentations may be superimposed, each with a different color/line style, a single segmentation can be superimposed at any given time, with the user having the ability to cycle through all the available segmentations through mouse clicks and/or keyboard shortcuts.

Figure 3:
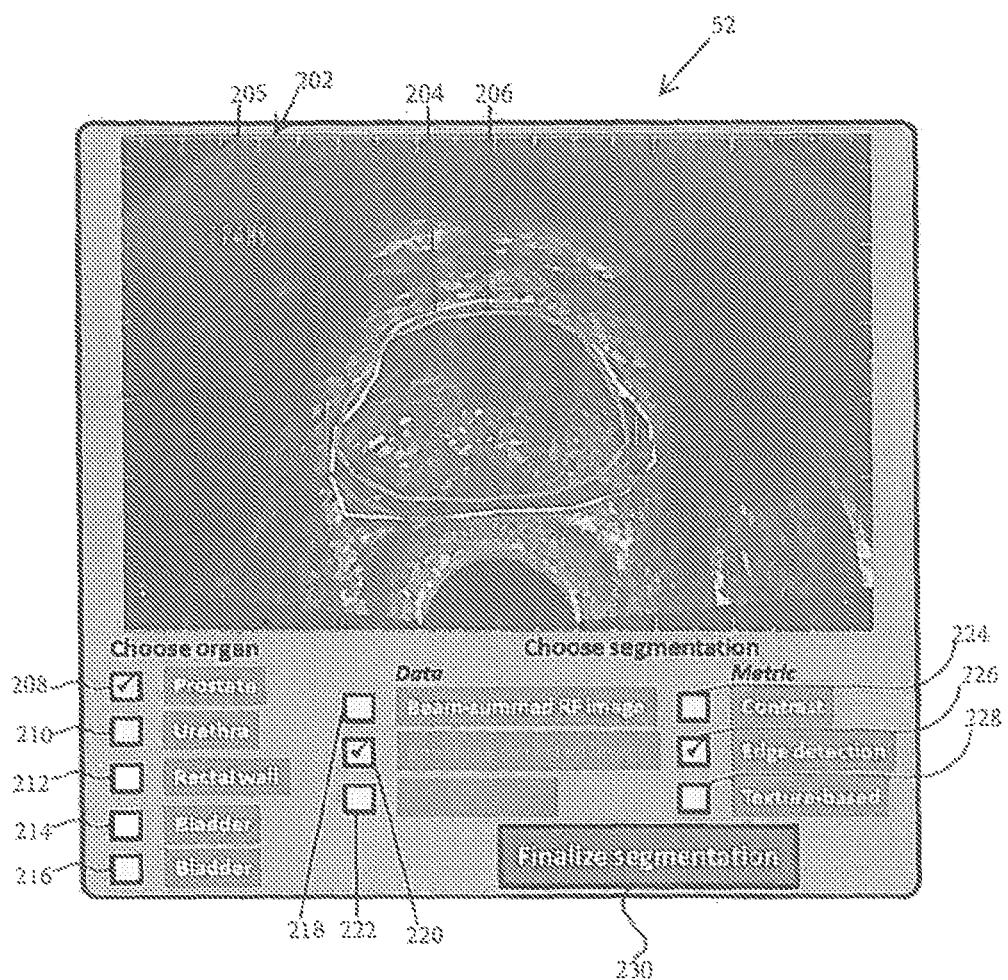
FIG. 3 is a diagram showing an illustrative graphical user interface for providing selection criteria and selecting a segmentation in accordance with one embodiment.

Referring to FIG. 3, an illustrative GUI 52 is shown in accordance with one exemplary embodiment. GUI 52 includes an image panel 202 where an image may include superimposed candidate segmentations 204, 206. Each candidate segmentation 204, 206 may be shown superimposed on a B-mode image 205. The candidate segmentations 204, 206 may all be shown concurrently or sequentially (or any combination thereof). The user may select input factors such as an organ to be segmented in check boxes 208, 210, 212, 214 and 216. The user may also select data on which segmentation is to be performed by selecting check boxes 218, 220, 222. The user may also select data on which segmentation metric is used to perform the segmentation by selecting check boxes 224, 226, 228. A final segmentation may be elected by presses button 230.

If the segmentations are performed in an automated manner, the segmentations resulting from each combination of input factors are shown to the user for selection of the 'optimal' segmentation. If the segmentations are to be manually performed by the user, the user is sequentially shown multiple images (e.g., the beam-summed RF image, the envelope detected image, B-mode images with and without filtering, etc.). The user performs a manual segmentation on the displayed image and has the choice of accepting or rejecting it. The user may select the automatic or manual modes of operation. After the optimal segmentation is selected by the user, it is finalized by clicking the 'Finalize segmentation' button 230.

It should be understood that the GUI 52 depicted in FIG. 3 is for illustrative purposes. The interface may be developed or extended as needed to include more functionality. The type and positioning of features on the GUI 52 may be changed or reorganized as needed or desired. Additional buttons or controls may be employed or some buttons or controls may be removed.

The present principles provide segmentation techniques, which find application in a variety of areas. Examples of accurate segmentation leading to accurate image registration find utility in areas such as, e.g., adaptive treatment planning for radiation therapy, intra-procedural therapy monitoring (e.g., brachytherapy, RF ablation), real-time biopsy guidance, etc. It should be understood that while described in terms of US imaging, the segmentation selection aspects in accordance with the present principles may be employed for other imaging modalities instead of US. For example, the segmentation selection may be employed for MRI, CT or other imaging modalities.

The present embodiments may be employed to provide enhanced organ segmentation capabilities that complement tracking technologies (e.g., EM tracking, ultrasound tracking) for interventional devices. Also, the segmentation methods and user interface can be integrated in existing commercial systems, without the need to provide user access to raw data. Automated segmentation capability in accordance with the present principles may be employed with improved accuracy on any of the clinically-available imaging systems, and in particular US imaging systems.

Figure 4:
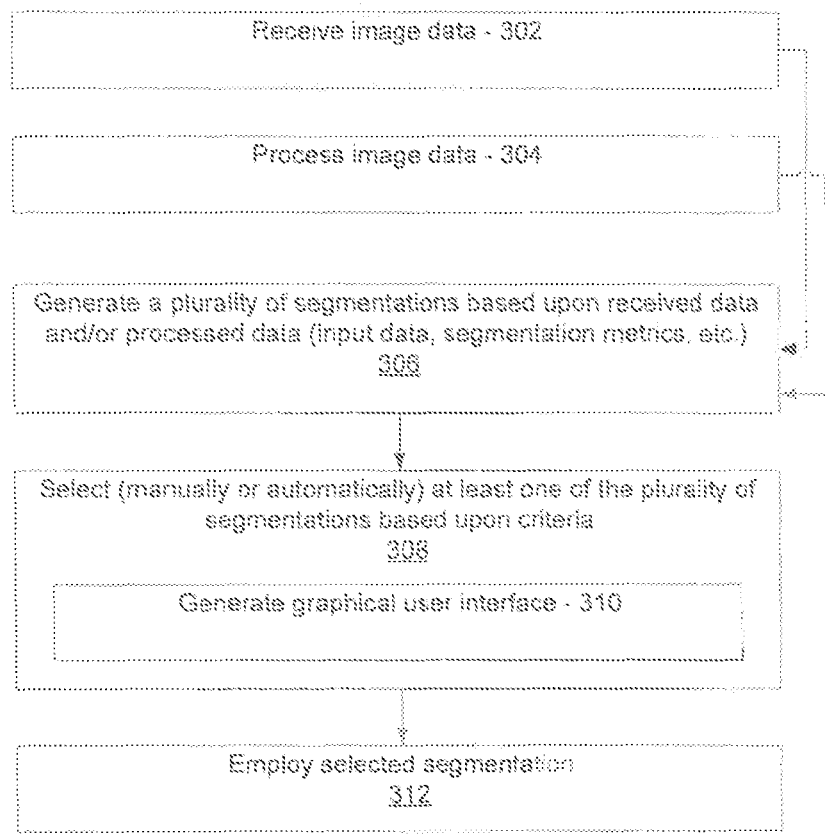
FIG. 4 is a flow diagram showing a segmentation selection method in accordance with illustrative embodiments.

Referring to FIG. 4, a method for segmentation selection is shown in accordance with illustrative embodiments. In block 302, imaging energy is received for imaging a subject. The imaging energy may include ultrasound, although other imaging modalities and energy types may be employed. In block 304, the received data is image processed to generate processed image data. The processed image data may include logarithmic compression, or other filtering or compression. The processing may include scan converting the data and/or B-mode processing. Other forms of processing are also contemplated.

In block 306, a plurality of segmentations are generated for the subject based on features or combinations of features of raw imaging data and/or processed imaging data. The raw imaging data may include raw radiofrequency data, envelope detection data, signal to noise ratio data, contrast data, texture data, edge detection data, etc. The processed imaging data may include a statistical model comparison, compressed data, converted data, B-mode processed display data, etc.

Segmentations may be generated based on raw data and processed data in different combinations to generate segmentations that differ from one another. Generating the plurality of segmentations may include generating the plurality of segmentations based on one or more combinations of input data and segmentation metrics. For example, one segmentation may be generated using a particular segmentation metric and a particular type of input data. The input data may include raw RF data, envelope detection data, B-mode display data, etc. The segmentation metric information may include statistical model comparison data, signal to noise data, contrast data, texture data, edge detection data, etc. Other segmentations may combine input data with segmentation metrics or combined aspects of the input data with aspects of the segmentation metrics. As an example, raw RF data may be combined with contrast and texture data to generate a segmentation. Other combinations are contemplated.

In block 308, at least one of the plurality of segmentations is selected that best meets a segmentation criterion. The selection criteria may include use desired aspects or automatic criteria. The features or combinations of features of the raw imaging data and/or the processed imaging data may be employed to generate the plurality of segmentations. The segmentation may be manually selected, which best meets user defined criteria or automatically selected based on programmed criteria (for example, contrast or pixel thresholds, a best fit image with a statistical model shape, etc.).

In block 310, a graphical user interface is generated and displays the plurality of segmentations. The segmentations are preferably displayed on a B-mode image (background), wherein the segmentation images are displayed concurrently or sequentially in accordance with a user preference.

In block 312, the selected segmentation is employed to perform an operative procedure or other task.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for optimal ultrasound-based organ segmentation (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A segmentation selection system, comprising:
 a transducer configured to transmit and receive imaging energy for imaging a subject, wherein received imaging energy includes imaging data;
 at least one signal processor configured to process the imaging data to generate processed image data;
 a segmentation module configured to generate a plurality of segmentations of the subject that differ from one another, wherein each of the plurality of segmentations is based on (i) different features of the imaging data and the processed image data or (ii) different combinations of features of the imaging data and the processed image data, wherein the imaging data includes at least radiofrequency data and envelope detection data; and
 a selection mechanism configured to select at least one segmentation of the plurality of segmentations based upon a criterion for performing a task.

2. The system as recited in claim 1, wherein the transducer includes an ultrasound transducer and the at least one signal processor includes a B-mode processor.

3. The system as recited in claim 2, wherein the imaging data further includes at least one of (i) signal to noise ratio data, (ii) contrast data, (iii) texture data and (iv) edge detection data.

4. The system as recited in claim 2, wherein the processed imaging data includes at least one of a statistical model comparison and B-mode display data.

5. The system as recited in claim 1, wherein the segmentation module generates the plurality of segmentations based on one or more combinations of input data and segmentation metrics.

6. The system as recited in claim 1, wherein the selection mechanism includes an image processor configured to automatically select the at least one segmentation of the plurality of segmentations based upon programmed criteria.

7. The system as recited in claim 1, wherein the selection mechanism includes graphical user interface that permits a user to select the features or combinations of features of at least one of the imaging data and the processed image data to generate the plurality of segmentations and to manually select the at least one segmentation.

8. The system as recited in claim 1, further comprising a display for displaying images of the plurality of segmentations and a B-mode image, wherein the images of the plurality of segmentations are displayed concurrently or sequentially on the B-mode image.

9. The system as recited in claim 1, wherein the segmentation module generates the plurality of segmentations of the subject that differ from one another further based on one or more segmentation metric.

10. The system as recited in claim 9, wherein the one or more segmentation metric comprise different segmentation metrics selected from the group consisting of statistical model comparison, signal to noise, contrast, texture, and edge detection.

11. The system as recited in claim 1, wherein the criterion is selected from the group consisting of: (i) whether a segmented volume of a selected at least one segmentation is at least a given volume, (ii) whether the segmented volume includes certain pre-annotated anatomical landmarks, (iii) whether the segmented volume differs from a mean population-based segmentation model by greater than a given percentage, and (iv) whether a segmented shape of the selected at least one segmentation differs from a mean population-based shape model by greater than a given percentage.

* * * * *